United States Patent [19]

Rexroad, Jr. et al.

[11] Patent Number: 6,020,203

[45] Date of Patent: Feb. 1, 2000

[54] CHROMATOGRAPHIC METHOD FOR DETERMINATION OF GLYCATED PROTEINACEOUS SPECIES IN BLOOD

[75] Inventors: James H. Rexroad, Jr., Kansas City, Mo.; Jimmie K. Noffsinger, Overland Park, Kans.; Bonnie A. Teeman; Claus-Peter Wawrzinek, both of Kansas City, Mo.

[73] Assignee: Primus Corporation, Kansas City, Mo.

[21] Appl. No.: 09/132,051

[22] Filed: Aug. 11, 1998

Related U.S. Application Data

[63] Continuation of application No. 08/309,795, Sep. 21, 1994, Pat. No. 5,843,788, which is a continuation of application No. 07/774,646, Oct. 15, 1991, abandoned, which is a division of application No. 07/708,871, May 31, 1991, abandoned, which is a division of application No. 07/280,016, Dec. 5, 1988, abandoned.

[51] Int. Cl.⁷ .......................... G01N 33/72; G01N 30/02
[52] U.S. Cl. ........................ 436/67; 436/66; 436/86; 436/87; 436/161; 210/656; 210/660; 530/413
[58] Field of Search .................... 436/67, 66, 86, 436/87, 88, 161; 530/413, 414; 210/198.2, 656, 660, 661

[56] References Cited

U.S. PATENT DOCUMENTS

| | | |
|---|---|---|
| 4,269,605 | 5/1981 | Dean et al. . |
| 5,135,650 | 8/1992 | Hjerten et al. . |
| 5,843,788 | 12/1998 | Rexroad, Jr. et al. . |

OTHER PUBLICATIONS

Chemical Abstracts CA 117:3504. Kitagawa et al., Anal. Sci. (1991), 7(Suppl., Proc. Int. Congr. Anal. Sci., 1991, Pt. 1), 195–8.

*Primary Examiner*—Jan Ludlow
*Attorney, Agent, or Firm*—Hovey, Williams, Timmons & Collins

[57] ABSTRACT

A method for continuous separation and analysis of glycated and non-glycated proteins in a blood sample by HPLC using a phenylboronic acid resin and a polyol as eluant.

3 Claims, 6 Drawing Sheets

Fig. 1.

Fig. 2.
MAIN MENU

Fig. 3.
SAMPLE DATA ENTRY

Fig.4.
SAMPLE ANALYSIS

Fig.5.
BREAK MENU

IDEALIZED BASELINE

Fig.9.

CHROMATOGRAPHIC METHOD FOR DETERMINATION OF GLYCATED PROTEINACEOUS SPECIES IN BLOOD

This is a continuation of Ser. No. 08/309,795 filed Sep. 21, 1994, now U.S. Pat. No. 5,843,788, which was a continuation of Ser. No. 07/774,646 filed Oct. 15, 1991, now abandoned, which was a division of Ser. No. 07/708,871 filed May 31, 1991, now abandoned, which was a division of Ser. No. 07/280,016 filed Dec. 5, 1988, now abandoned.

BACKGROUND OF THE INVENTION

1. Field of the Invention

The present invention is broadly concerned with an improved method for the quantitative determination of glycated proteins in a liquid sample such as blood or other body fluids, extracts or emulsions (e.g., urine) containing both glycated and nonglycated protein fractions. More particularly, it is concerned with such a method which makes use of spectrophotometric quantitation employing balanced mobile phases during the analysis which absorb as background substantially equal quanta of light. In this fashion, the analysis can be conducted using automated equipment and with the complete elimination of the need for blanking of the spectrophotometer. A novel electronic control of the automated analysis is also disclosed.

2. Description of the Prior Art

The measurement of glycated protein in the blood of a patient suffering from diabetes mellitus provides an attending physician with a means for assessing blood sugar control over different periods of time. As a consequence, considerable research has been done in the past to develop accurate, rapid analyses for glycated proteins. In order to be truly effective, however, such methods should also be capable of measuring the glycated protein content of both hemoglobin and plasma (serum) proteins. This stems from the fact that the percentage of glycated hemoglobin in a sample is a measure of mean blood sugar concentrations for the preceding 45 to 60 days, whereas the percentage of glycated plasma protein reflects blood sugar concentrations over a shorter period, approximately 1–3 weeks prior to analysis.

It is known that non-enzymatically glycated proteins such as hemoglobins and circulating plasma or serum proteins differ from nonglycated species by the attachment of sugar moieties to the proteins at various binding sites by means of a ketoamine bond. Glycated proteins thus contain functional groups (sometimes reported as 1,2-cis-diol groups) not found in nonglycated proteins. The presence of such functional groups thus provides a basis for separation of glycated and nonglycated proteins.

One known technique for separating glycated and nonglycated protein fractions is known as boronate affinity chromatography. This analysis relies on the fact that borates or boronates, such as m-aminophenylboronic acid (PBA), can under certain conditions, bond with the functional groups in glycated proteins. The bonds in the resulting complex are reversible in aqueous solution. In the typical chromatographic system, the boronate is immobilized on a support medium in a chromatographic column. A solution containing the substance under analysis, such as hemoglobin or plasma (serum), is applied to the column, wherein the glycated components bond with the boronate. Nonglycated components are washed out of the column with a suitable buffer solution, then eluated from the column and collected separately. Eluation of the glycated components is achieved by means of either: 1) a buffer solution containing a competing polyol, which replaces the protein in the boronate complex, or 2) a buffer or acid solution of low (below neutrality) pH.

A number of secondary factors, such as interactions between boronates and amines or carboxyls, influence the chromatographic separation. Complex molecules such as proteins also engage in hydrophobic, ionic, hydrogen-bond, and charge-transfer interactions. The need to design chromatographic systems which maximize the specific binding of boronates with diol-containing glycated proteins is therefore complicated by the need to also minimize the binding of nonglycated proteins through nonspecific interactions. Many factors such as buffer composition, molarity, ion content, ligand concentration and pH are known to influence the boronate affinity chromatographic separation of glycated and nonglycated proteins.

Glycated and nonglycated proteins separated chromatographically are commonly quantitated spectrophotometrically. For hemoglobin quantitation, the spectrophotometer is set to measure the absorbance of light in or near the "Soret region" (413–415 nanometers), which is the range of peak absorbance for hemoglobin. For plasma (serum) protein quantitation, the spectrophotometer is set to measure the absorbance of light in the 280 nanometer range, at which the proteins show peak absorbance. Of course, other wavelength determinations can also be maintained using known chromagens in the eluates. The buffer solution used to elute the non-glycated components is first placed in the light path of the spectrophotometer. The spectrophotometer is then adjusted so that zero absorbance is displayed on the scale or readout. This procedure, called a "blank", corrects for the background absorbance of the contents of the buffer solution. The next step is to place the non-glycated protein-containing buffer solution in the light path of the spectrophotometer and record the absorbance of light. By virtue of the "blanking" procedure, any increase in the absorbance of light by the protein-containing solution is due entirely to the protein content.

The same procedure is used for the eluate containing the glycated components; that is, the spectrophotometer is first "blanked" with the elution buffer solution in the light path, after which the increase in absorbance of the protein-containing buffer is recorded. Quantitation is then achieved by calculation. The increase in absorbance over the "blank" solutions of the protein-containing solutions is directly proportional to the protein content. The calculation also takes into account the dilution of the proteins by the buffer solutions. The result of this calculation is the expression of the glycated components as a percentage of the whole, e.g., "10% glycated hemoglobin" or "14% glycated plasma proteins."

The above procedure, although somewhat effective in yielding accurate hemoglobin protein analyses, is generally inaccurate or imprecise in serum protein analyses, and moreover is less suited for commercial laboratories because the protocol is very time consuming and costly. Thus, the need to individually collect and subsequently blank each of the eluates presents a significant drawback in the context of multiple analyses in a large laboratory.

SUMMARY OF THE INVENTION

The problems outlined above are in large measure solved by the present invention, which provides an improved analytical method specifically designed to overcome the problems associated with the application of boronate affinity methods in the measurement of glycated proteins in one aspect of the invention, use is made of automated chromatographic equipment together with specially designed mobile phases which are spectrophotometrically balanced, i.e., each absorbs substantially the same amount of light at the wavelengths of interest, while still giving the necessary separation of the nonglycated and glycated protein fractions. This eliminates inherent integrator error found to occur when using automated equipment and conventional mobile phases, thereby giving much greater accuracy in the analysis. In addition, greatly improved electronic control for the automated equipment is provided, which essentially eliminates multiple operator inputs over the course of analyses.

In more detail, the method of the invention is concerned with analyzing a liquid sample containing both glycated and nonglycated protein fractions and is broadly based upon the concept of boronate affinity chromatography. In the method, a support (preferably vinyl polymer particles, although other types of synthetic resin supports can be used, so long as they are capable of withstanding the broad pH ranges and pressure conditions of the analysis) is employed having complexible hydroxyboryl moieties bound thereto, typically by covalent coupling. The support is then contacted with a liquid sample to be analyzed, along with an initial mobile phase or transport solution (mobile phase A) for the nonglycated protein fraction. The glycated fraction complexes with the bound hydroxyboryl moieties, while the transport solution and nonglycated proteins are passed from the column as a first analyte and spectrophotometrically analyzed at the appropriate wavelength.

In the next step, an eluant (mobile phase B) is passed through the column to separate the glycated proteins from the support. A second analyte comprising the eluant and separated glycated proteins is then spectrophotometrically analyzed.

Very importantly, the transport solution and eluant are "balanced" so that otherwise inherent errors observed in high pressure liquid chromatographic (HPLC) analysis are largely eliminated. That is to say, integrator errors arising from greatly different absorbances by the respective solutions are essentially or largely eliminated, thereby enhancing the accuracy of the final quantitative results. In practical terms, the transport solution and eluant are balanced such that, in the quantitative HPLC determination of glycated protein in a 0.5 ul. liquid test sample containing 6 to 8 g./dl. of total protein and a glycated fraction amounting to 12–15% of the total protein of the test sample, the calculated signal to noise ratio equal to or above about 20 (the determination being carried out at a desired wavelength). In this test, the "signal" is the height of the absorbance peak produced by the glycated fraction of the test sample, whereas the "noise" is the greatest distance of deviation observed when a blank sample of the transport solution is measured at the desired wavelength and at otherwise identical test conditions. In this regard, both the absorbance peak height and deviation distance are measured relative to an idealized baseline established by the absorbance of the transport solution at the desired wavelength. Such idealized baseline is established by a line drawn horizontally on an HPLC absorbance graph from the point of injection of the blank transport solution to the end of the glycated fraction absorbance peak. The idealized baseline thus represents the idealized absorbance of the transport solution only.

While in preferred forms the HPLC analyses of the invention changes in mobile phase composition carried cut in "stepwise gradient" fashion, use can be made of a "continuous gradient" system. In such a system, any absorbance difference between the transport mobile phase and the eluant would ideally result in a smooth continuous curvature in the baseline. Noise in such a system would be defined as any abrupt deviation from a smooth continuous curvature. Even in this situation the defined signal to noise ratio should be at least 20.

Broadly speaking, the mobile phase A or transport solution is preferably a mixture of buffers and ions designed both to condition the column for binding of glycated proteins, and to enhance the binding of those proteins. HEPES, ammonium acetate, glycines, phosphates, taurine and related buffers are all suitable for conditioning the column. This solution may also advantageously contain sodium chloride rather or in addition to the more commonly employed divalent magnesium chloride for enhancing the binding of glycated proteins.

The mobile phase B eluant is a mixture of ions and competing polyols for removing the glycated proteins bound to the column. In order to elute the glycated proteins, the polyol or other competing compound should have a greater mass transfer affinity for the binding sites than the glycated proteins. In practice, sodium chloride is used as the ion source, whereas competing polyols may comprise mannitol, dulcitol, xylitol, or TRIS. Compounds containing carboxyl groups, such as sodium citrate/citric acid are also suitable. The glycated proteins can also be removed from the column by changing the conditions in the column such as by lowering the pH by means of a mobile phase containing an acid, e.g., citric or acetic acid.

The final solution, mobile phase C, is designed to remove the competing polyol or other compound from the column in preparation for reequilibration. Aqueous sodium acetate is suitable as the mobile phase C, as is TRIS or NaCl.

The preferred HPLC apparatus includes an analytical column in the form of a glass, stainless steel or plastic tube having endmost fittings. The column is filled with polymer particles of approximately 3–20 microns (preferably 10 microns) in diameter having pores or openings of about 300–1,000 Å in diameter. PBA is bonded to the polymeric support by covalent coupling. The filled column is distributed by the TosoHaas Company of Philadelphia, Pa. under the designation "Boronate-5PW".

In operation, the transport solution or mobile phase A is pumped through the column at a rate of 1 milliliter per minute (minimum pressure setting, 20–30 bar, maximum pressure setting, 100 bar) for a time sufficient to fully equilibrate the PBA, this usually taking about 1.0–2.0 minutes. 2–25 microliters of diluted sample are next injected into the column along with continued passage of the transport solution, in order to wash the nonglycated fraction through the column. This takes approximately 0.4–1.0 minutes. The transport solution and nonglycated protein fraction are then passed through the detector where the absorbance at the selected wavelength is measured.

After all nonglycated proteins have passed through the detector, the eluant (mobile phase B) is passed through the column eluting the glycated fraction. After the glycated components have passed through the detector and the absorbance detected (approximately 1½–3 minutes), the mobile phase C is pumped through the column to remove all traces of the eluant. This last step takes approximately 1–2 minutes, whereupon the initial phase is again pumped through the column for reequilibration thereof.

The spectrophotometric detector is zeroed at 5% of scale, that is the absorbance of light at the beginning of operation is adjusted to 5% of scale so that changes of absorbance to less than starting conditions are recorded.

The present invention also encompasses a method of operating a liquid chromatograph in order to eliminate the need for a highly skilled and dedicated operator. This aspect of the invention includes the provision of an electronic memory device, typically a floppy disk, which includes the required electronically retrievable instructions for operating the liquid chromatograph. These instructions may ask for data entry including, for example, specific sample identification data for each sample to be analyzed, a selection of which analytical method is to be used if more than one is stored on the disk, and an actual command to begin the procedure.

With completion of the data entry, the operating instructions take over in order to initialize the liquid chromatograph including equilibration of the column in accordance with the selected method and operating instructions. The samples are then successively analyzed according to the selected method included as part of the pre-programmed instructions. During the analyses, the computer then produces output along with analysis results and corresponding sample identification data. The liquid chromatograph including the column is then placed in the standby or shutdown mode in accordance with the operating instructions.

DESCRIPTION OF THE PREFERRED EMBODIMENTS

As indicated above, prior known attempts at using boronate affinity chromatography for glycated protein analyses have been difficult and time consuming, and not at all suited for commercial utility. In initial attempts to overcome these problems, use was made of continuous, automated HPLC equipment developed for commercial laboratory use. One such unit is manufactured by the Hewlett Packard Company, and is commercialized under the designation "HP 1090". This unit includes fittings adapted to receive a chromatographic column, automatic sampling and column injection means, and multiple mobile phase reservoirs, and is coupled with a computing integrator (e.g., models HP 3393 or HP 3396).

In the use of such automated equipment for glycated protein analyses, a boronic acid such as PBA was immobilized on a suitable support. In particular, an analytical column in the form of a glass, stainless steel or plastic tube (4.1 mm I.D.×3.5 cm length) with fittings on each end designed to attach to tubing which carries the multiple mobile phases, is filled with the preferred support, to which the PBA has been bound by conventional means.

A total of three separate, conventional mobile phases were used in the automated equipment, these being denominated as phases A, B, and C. The first phase (A) was designed to enhance the binding of glycated components to the boronate matrix by converting the hydroxylated moieties to the tetrahedral anionic form thereof. This starting phase also served as a transport medium for nonglycated proteins during the analysis. Common buffers include ammonium salts, phosphates, glycines, morpholine, taurine and HEPES (N-2-hydroxyethylpiperazine-N-2ethanesulfonic acid). Ionic strength and pH may be adjusted to minimize secondary interactions between the boronate column packing and the protein. Magnesium ions, usually in the form of magnesium chloride ($MgCl_2$), may be added to reduce ionic effects without causing hydrophobic bonding. The most commonly employed starting buffer contains, per liter, 250 mmol ammonium acetate, 50 mmol $MgCl_2$, pH adjusted to between 8.0 and 9.0. Sodium azide or other preservatives were employed to enhance shelf life.

The second mobile phase (B) was designed to elute the glycated components from the column, most frequently by means of a competing polyol which displaces the glycated components from the binding sites of the column support. The mobile phase B was a mixture of polyol and buffering compound, but a solution of polyol alone is sometimes employed. The most common second elution buffer consisted of, per liter, 100 mmol TRIS (tris(hydroxymethyl) aminomethane), 200 mmol sorbitol, 50 mmol EDTA (ethylenediaminetetraacetic acid), pH 8.0–8.15. Again, trace amounts of preservatives such as sodium azide are normally present.

Another technique for elution of the glycated components employed a mobile phase of low (below neutrality) pH. The most frequently used solution was sodium citrate/citric acid, pH 4.5.

Column regeneration was achieved by means of a third mobile phase (C), which removed the competing polyol or carboxyl from the binding sites of the column support by means of an acid. 20% acetic acid was normally employed in this context.

In such initial tests, the PBA column was equilibrated by passing sufficient mobile phase A through the bed to ionize the boronate. At this point a sample containing hemolysate or plasma (serum) proteins (prepared by conventional means) was introduced into the column with a small amount of the starting buffer, mobile phase A. Sufficient mobile phase A was then passed through the column to completely wash out all nonglycated components of the sample and this was then passed through the spectophotometric detector associated with the apparatus, and analyzed using light of the particular wavelength appropriate for the compounds of interest, normally either 413 nm or 280 nm.

Glycated components were next eluted from the column with the second mobile phase (B), which was passed through the column bed in sufficient amounts to remove all glycated components. This eluate was then passed through the detector for spectrophotometric analysis, at the same wavelength used in connection with the first eluate.

The separately analyzed eluates respectively containing the nonglycated and glycated protein fractions were quantitated on a conventional chromatogram produced by the integrator and printout device forming a part of the equipment. Such chromatograms ideally include a zero or baseline which is a measure of the absorbance of the starting mobile phase (A), a first peak representative of the nonglycated protein fraction, and a second peak corresponding to the glycated fraction.

Finally, the column was regenerated by washing with the final mobile phase (C) to remove the competing polyol or carboxyl. After such regeneration, the column was reequilibrated with the starting mobile phase (A).

While such straightforward chromatographic analyses using automated equipment of the type described was attempted, a number of practical difficulties were encountered. Most significantly, the described automated procedure using conventional mobile phases inherently leads to large quantitative errors, thereby effectively defeating the entire purpose of the procedure. In particular, in order to correctly measure the increase of the detector signal (represented by the area under the peak in the chromatogram) that is due only to the analyte, integrators have certain built-in capabilities designed to deal with background interference on shifting baselines. For example, an integrator can be pre-set to skim a small peak from the downslope of a larger peak, or to end a peak at a certain time. However, the performance characteristics of a boronate affinity column employed with conventional mobile phases preclude the use of these built-in functions.

The problem arises because the analyte is released nearly instantaneously from the column upon contact with mobile phase B. As a result, mobile phase B and the analyte exit the column almost simultaneously. At the point of exit the increase in detector signal is recognized by the integrator as the beginning of the peak, and the integrator begins recording. If mobile phase B absorbs more light of the pre-set wavelength than did mobile phase A, the signal strength does not approach the zero or baseline setting established by mobile phase A. The integrator interprets the high signal strength caused by mobile phase B as a continuation of analyte from the column, and adds this signal, incorrectly, to the area under the analyte peak.

One possible way to counter this integration problem is to preprogram the integrator to end the peak at a certain time, e.g. 4 minutes after injection. This approach is unsatisfactory because different samples contain different amounts of analyte, and thus, create peaks of differing widths. No preprogrammed time for this integrator function will serve for accurate integration of the variety of analyte concentrations encountered in actual testing.

Figure 6:
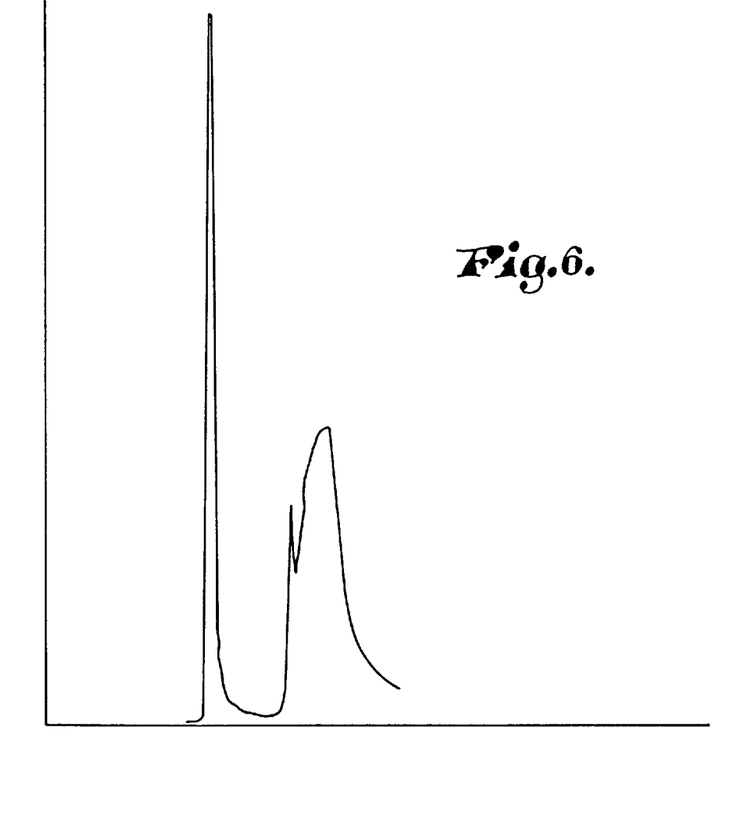
FIG. 6 is a chromatogram produced by automated HPLC equipment as a result of an analysis of a glycated serum protein sample using conventional mobile phases.
Figure 7:
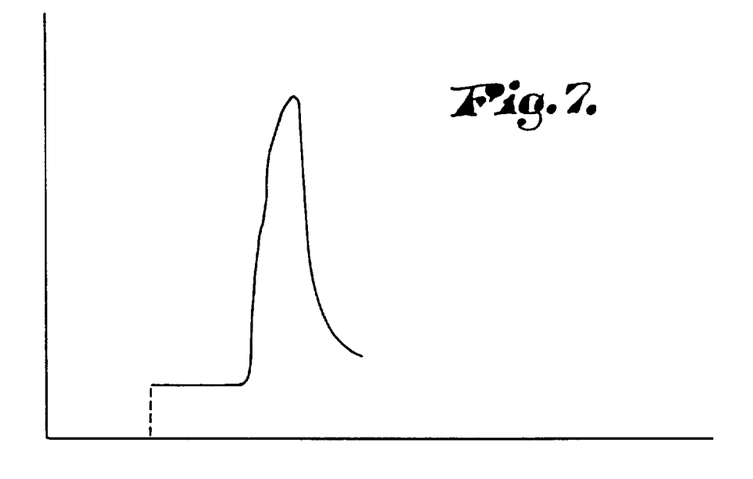
FIG. 7 is a chromatogram produced by automated HPLC equipment as a result of an analysis of blank conventional mobile phases.

These problems are graphically depicted with reference to FIGS. 6 and 7. In particular, FIG. 6 illustrates a chromatogram developed during an analysis of a pooled sample of serum protein taken from a plurality of normal (i.e., non-diabetic) individuals. The chromatogram was produced using the described automated equipment with conventional mobile phases. The inherent integrator error is evident from a study of the chromatogram, and particularly the second peak thereof. The analysis gave a result indicating that 71.8% of the sample was glycated protein. This is known to be greatly in excess of the true glycated protein level of the sample.

The gross error reflected in FIG. 6 is explainable with reference to FIG. 7, which depicts a chromatogram developed using the identical equipment and operating protocol, but analyzing only the conventional mobile phases A and B. The large peak evident in this chromatogram is a result of the unbalanced nature of the mobile phases, and the consequent integrator error.

In short, attempts at using automated HPLC equipment and typical mobile phases were found to be unworkable.

An additional problem with conventional HPLC equipment stems from the electronic control associated therewith, in that such control (software) is relatively cumbersome and difficult to use. That is to say, the control software requires multiple inputs by the operator prior to and/or during the course of the analysis, which in turn means that the equipment must be constantly attended to by skilled personnel.

More specifically, a highly trained and skilled operator is required in order to initialize the liquid chromatograph and to equilibrate the column. Furthermore, the operator must be in attendance and sufficiently skilled and trained in order to place the liquid chromatograph in an end-of analysis mode after samples have been analyzed. In other words, the operator must be in attendance to place the liquid chromatograph and the column in a stand-by mode which typically involves setting up the system or instrument to run the wash solution, through the column, or to shut down the liquid chromatograph by additionally shutting off the solvent delivery system, and possibly washing the column also. Even though certain programs are available for controlling the actual chemical method for analyzing the sample, the attending operator must still be highly skilled and trained in order to perform the other necessary functions for setting up the liquid chromatograph and placing it in an end-analysis mode.

A principal advantage of the present invention is that the problems inherent in the use of conventional HPLC equipment and mobile phases for glycated protein analyses have been overcome. Actual testing demonstrates that the invention is capable of giving very accurate glycated protein determinations, while at the same time making the procedure streamlined and easy to use.

Figure 1:
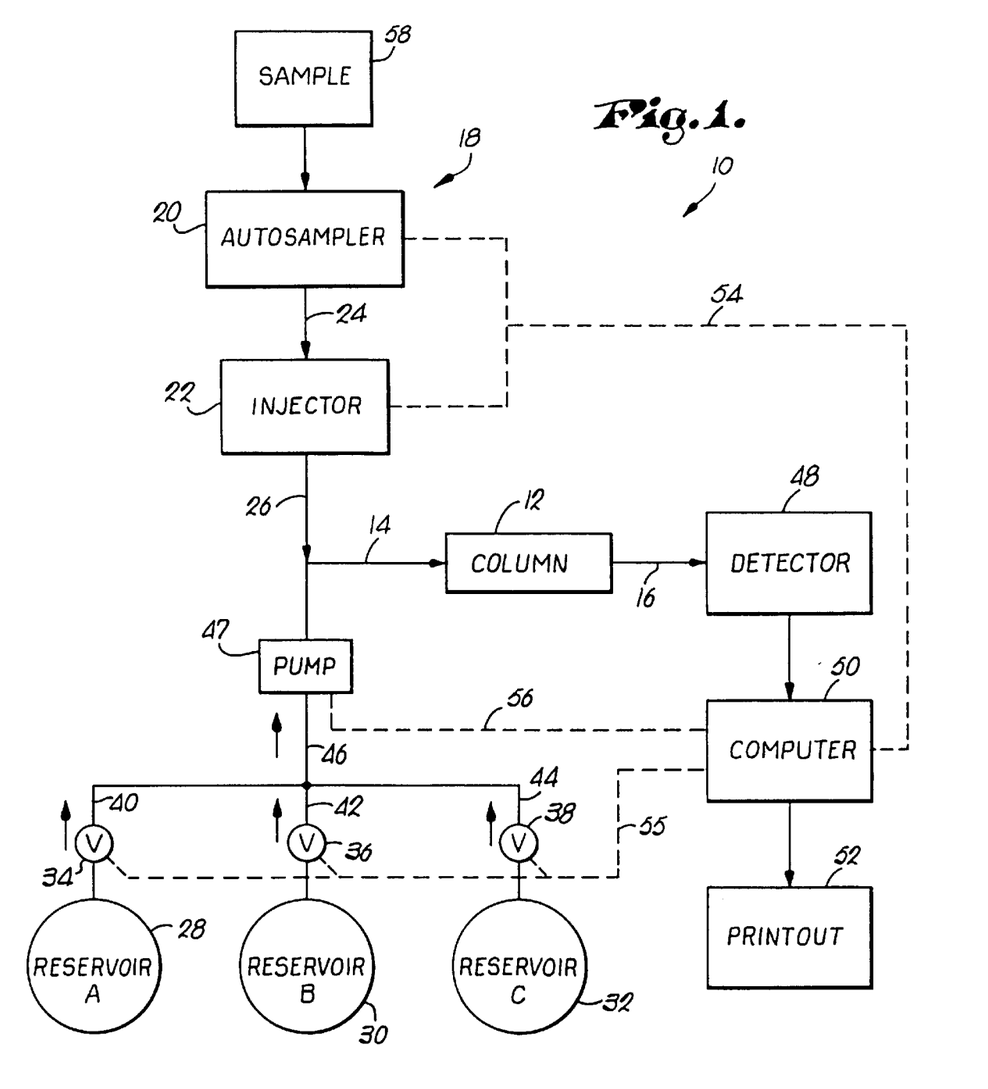
FIG. 1 is a schematic representation of the preferred apparatus used in performing the analytical methods of the invention.

Turning now to FIG. 1, an automated chromatographic device 10 useful in the invention is schematically illustrated. The device 10 includes a chromatographic column 12 having an input line 14 coupled to one end thereof, with an output line 16 connected to the opposing end. A sample injection system 18 is also provided including an autosampler 20 and injector 22, interconnected by means line 24. The injector is in turn connected to input line 14 of column 12, via line 26.

The device 10 further includes a total of three reservoirs 28, 30, and 32 respectively adapted for holding the mobile phases A, B, and C. Three valves 34, 36, and 38 are respectively coupled to an associated reservoir 28, 30, and 32, with an output line 40, 42 or 44 leading from a respective valve to a common output line 46. The line 46 is in turn connected with input line 14 of column 12, and has a pump 47 interposed therein. Alternately, use can be made of a single switching valve in place of the valves 34, 36, and 38.

The device 10 also includes a spectrophotometric detector 48 of conventional design which is connected with output line 16 from column 12. The detector 48 is in turn electrically coupled with an integrating computer 50 which is connected to and controls a chart printout device 52. Electrical leads schematically illustrated as at 54, 55 and 56 respectively couple computer 50 with the autosampler 20 and injector 22, with the operations (not shown) of the valves 34–38, and with the motor (not shown) of pump 47. This allows complete control of the injection system 18 and the reservoir pump via computer 50.

The device 10 is preferably a commercially available Hewlett Packard Model HP 1090 automated chromatograph.

The device 10 is provided with special software for the control of computer 50, such being described in detail hereinafter.

As is apparent from the foregoing discussion, a sample 58 is injected via system 18, and the entire device 10 is then controlled by way of computer 50 to perform the entire analysis on an automated basis. The computer 50 together with the printout device 52 correspondingly develops a chromatogram, and measures the area under the analyte peaks, thereby providing an accurate protein analysis.

Preparation of sample 58 is essentially conventional. In the case of a blood sample, venous blood (typically 3 ml minimum) is collected via either venipuncture or fingerstick (50–100 ul). Freshly collected blood is mixed with sufficient anticoagulant, such as EDTA or heparin, to prevent clotting.

Two variations of sample preparation are used for the glycated hemoglobin test. Both involve the preparation of a "hemolysate" or solution of blood in which the RBC cell membranes have been lysed or ruptured. In the first variation, whole blood is diluted 1:100 in purified water or other lysing agent, which ruptures the RBC membranes. In the second variation, the blood sample is centrifuged, which separates the plasma from the cells. The plasma is removed and the hemolysate is prepared from the packed RBCs by diluting them 1:200 in purified water or other lysing agents. Minimum volume of the hemolysate required for injection is 2 microliters.

There are also two variations of sample preparation for the glycated serum (or plasma) protein test, with the key difference between the two being the presence or absence of an anticoaguiant. When an anticoaguiant is used, the blood sample is centrifuged and the plasma is removed for testing. When no anticoagulant is used, the blood sample is allowed to thoroughly clot, which takes at least an hour before centrifugation. After centrifugation, the serum is removed for testing. Then either the serum or plasma is diluted 1:10 in purified water, saline, or in mobile phase A. Minimum volume of diluted plasma or serum required for injection is 2 microliters.

Using these sample preparation techniques to give diluted sample solutions, with the previously mentioned column injection levels of 2–25 microliters, the range of analyte applied to the HPLC column is from 3.38–181.3 micrograms.

Hemolysates or diluted plasma or sera are transferred to glass or plastic sample vials, which are specially designed to fit the autosampler 20. A metal cap with a flexible septum is attached by means of a crimping tool to cover the top of the vial.

The most preferred mobile phase A designed for introduction into reservoir 28 is an aqueous solution containing 0.1 M glycylglycine, 0.3 M sodium chloride, 1% ethyl alcohol, and sufficient sodium hydroxide to bring the pH of the solution to about 8.5. An antimicrobial preservative can also be added if desired. Mobile phase B is likewise an aqueous solution and includes 0.1 M mannitol, 0.15 M sodium chloride, and 5% ethyl alcohol; an antimicrobial preservative can also be added. Finally, the mobile phase C is an aqueous solution including 0.2 M TRIS (tris (hydroxymethyl)aminomethane), 0.5 M sodium chloride and sufficient hydrochloric acid to give the system a pH of about 8.5. Again, an antimicrobial preservative can be added if desired. As described above, various changes can be made in both the proportions and specific components of these mobile phases, the important factors being that the solutions be capable of separating the glycated and nonglycated fractions in the chromatograph, while also being spectrophotometrically balanced as described above.

Referring again to FIG. 1, computer 50 typically includes an output printer 52 coupled therewith, a data entry keyboard, and a floppy disk drive for receiving a memory device such as a floppy disk and for electronically retrieving instructions stored thereon. As those skilled in the art will appreciate, the memory device can also include a so-called "hard disk," compact optical disk, magnetic tape or any type of device on which electronically retrievable instructions can be stored.

In the preferred embodiment, more than one analytical method for operating liquid chromatograph 10 may be stored on the floppy disk such as the methods described above for analyzing liquid samples containing both glycated and nonglycated protein fractions. The utility of the preferred embodiment is not so limited, however, but rather is enhanced by the ability to include instructions for virtually any analytical method for operating the liquid chromatograph. As an alternative, a separate memory device may be provided for each analytical method which can advantageously form a library of complete methods for operating liquid chromatograph 10.

In practice, the operator first ensures that the liquid samples to be analyzed are placed into autosampler 20, that reservoirs 28–32 contain the proper mobile phases, and that the proper column 12, specific to the analyses to be performed, is in place. The operator then places the selected disk in the disk drive and boots up computer 50.

Figure 2:
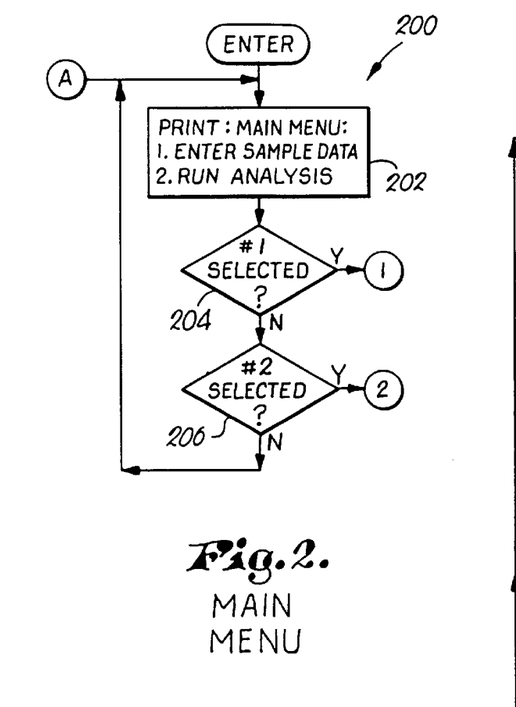
FIG. 2 is a computer program flow chart illustrating the main menu portion of the program for operating the liquid chromatograph.
Figure 3:
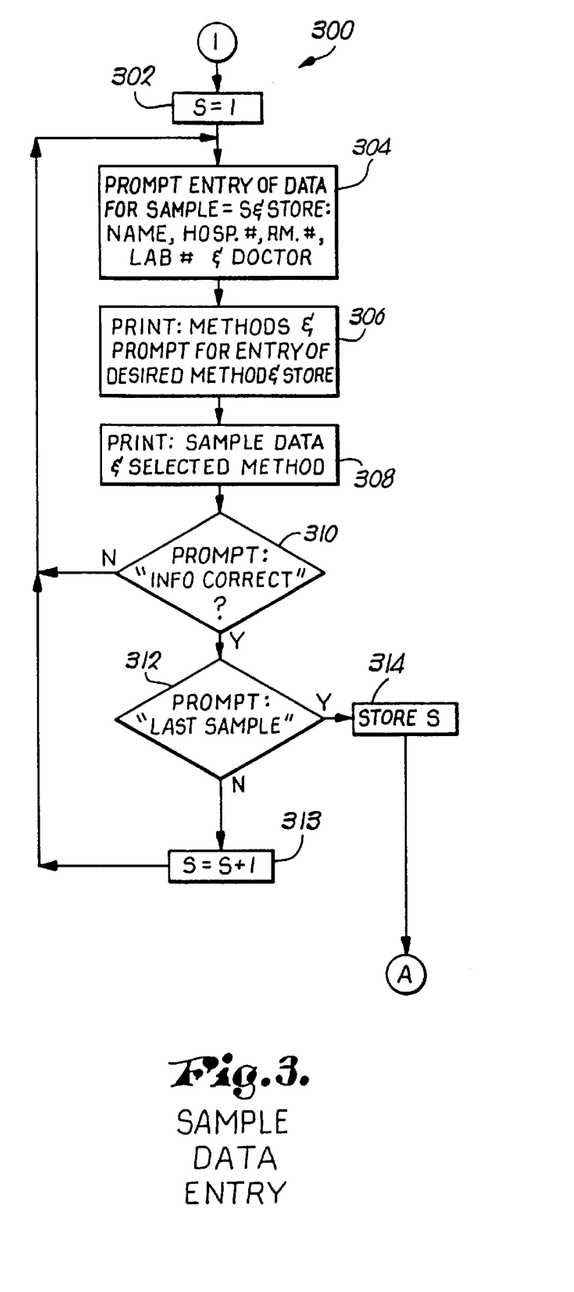
FIG. 3 is a computer program flow chart illustrating the sample data entry module of the operating program.
Figure 4:
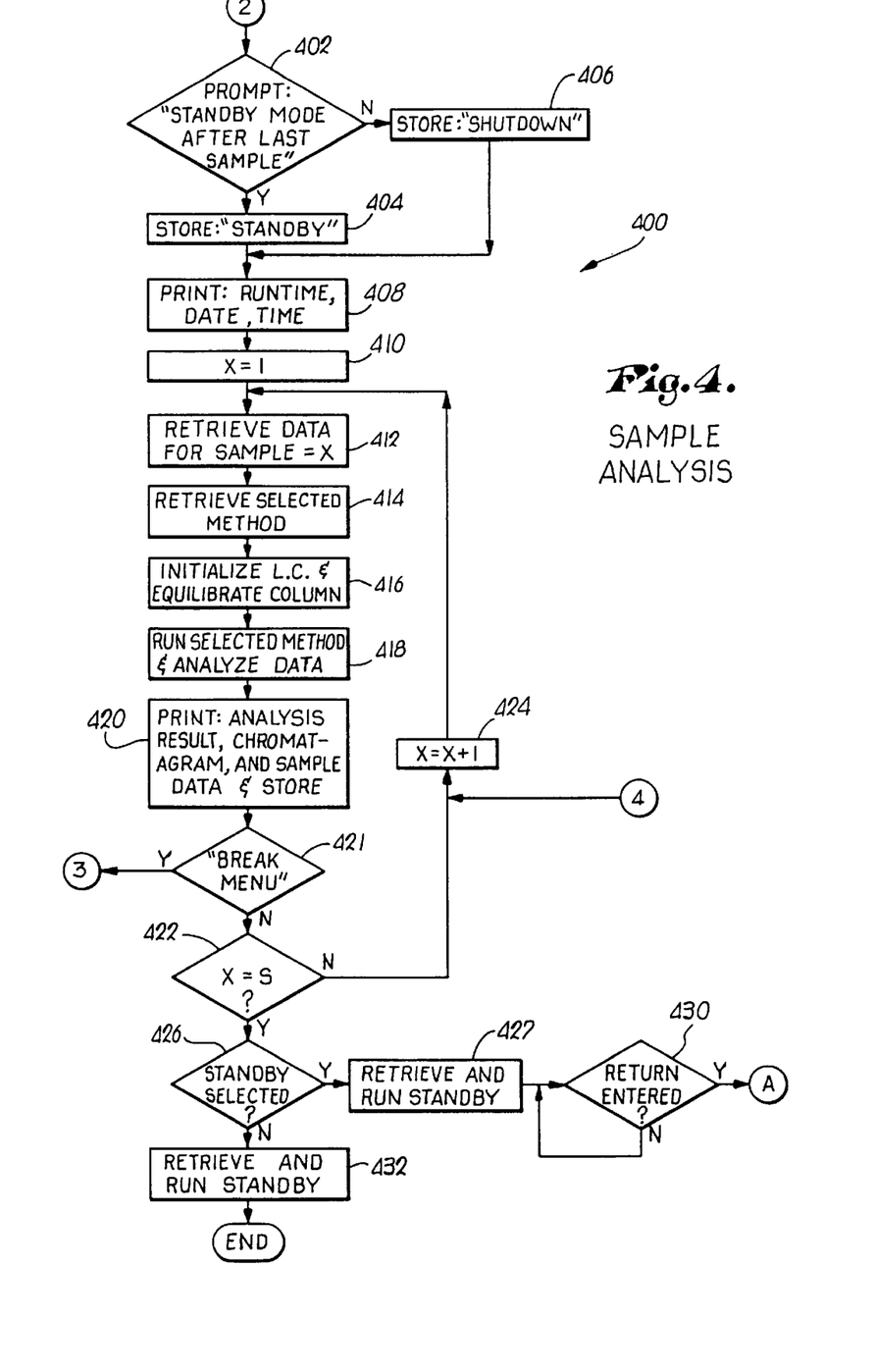
FIG. 4 is a computer program flow chart illustrating the sample analysis module of the operating program.

FIGS. 2, 3, 4, and 5 are computer program flow charts illustrating the preferred operating program on the floppy disk. The program initially enters menu module MAIN MENU 200 (FIG. 2) at step 202 which displays the main menu and prompts the operator to select an item therefrom. In the preferred embodiment, the main menu includes a selection for SAMPLE DATA ENTRY module 300 (FIG. 3) and SAMPLE ANALYSIS module 400 (FIG. 4). As those skilled in the art will appreciate, the operating and accounting summaries of completed analyses, methods available on other floppy disks, reagents (mobile phase), column selections, and so forth.

The operator then selects one of the menu choices presented on the output in step 202 by way of the data entry keyboard. The program then moves to step 204 which asks whether the first menu item was selected. If yes, the program moves to SAMPLE DATA ENTRY module 300. If no, the program moves to step 206 which asks whether the item selected was the second menu item. If yes, the program moves to SAMPLE ANALYSIS module 400.

If the answer in step 206 is no, which might happen in the event of an incorrect keyboard entry, the program loops back to step 202 to again display the main menu and prompt the operator to select one of the items therefrom.

Normally the operator initial selects the first item on the main menu which is SAMPLE DATA ENTRY module 300 (FIG. 3). This module prompts the oderator to enter specific data corresponding to each of the samples. Module 300 enters at step 302 which sets software variable S equal to I which corresponds to sample No. 1. The program then moves to step 304 which prompts the operator on the display screen to enter in sequence specific data concerning sample "S". This sample data preferably includes the patient name, the hospital, the patient room number if applicable, laboratory identification number, and the requesting physician.

The program then moves to step 306 which displays the analytical methods available on the selected disk. As those skilled in the art will appreciate, the number of methods included on the memory device will depend, in part, upon the memory capacity of the device.

The program then moves to step 308 which prints the sample data and selected method on the printer and prompts the operator in step 310 to indicate whether the displayed information is correct. if no, the program loops back to step 304 to start over again.

If the answer in step 310 is yes, the program moves to step 312 which prompts the operator to answer whether the sample data just entered corresponds to the last sample to be run. If no, the program moves to step 313 which increments variable S for the next sample and loops back to execute steps 304 through 312 for the next sample in the series.

When sample data has been entered for each sample in the series, the operator enters yes in step 312 and the program moves to sted 314 to store the value of variable S which represents the total number of samples. The program then exits module 300 and loops back to step 202 of MAIN MENU module 200 (FIG. 2).

After the sample data has been entered, the operator typically selects the second item on the main menu, the answer in step 206 is yes, and the program goes to SAMPLE ANALYSIS module 400 (FIG. 4). Module 400 enters at step 402 which prompts the operator to enter data on the keyboard indicating the desired end-of-analysis mode for the liquid chromatograph and column after the last sample has been analyzed. More specifically, and in the preferred embodiment, step 402 prompts the operator to enter whether the liquid chromatograph including column 12 is to be put in "standby" mode after the last sample has been analyzed. If the operator enters yes, the program moves to step 404 which stores the bit notation for the standby mode. If the answer in step 402 is no, the program moves to step 406 which stores the bit notation for shutdown after the last analysis.

After steps 404 or 406, the program moves to step 408 which prints the run time, date, and real time on the printer.

The program then moves to step 410 which sets the software variable "X" equal to 1, which corresponds to the first sample to be analyzed and then to step 412 which retrieves the sample data entered during execution of submodule 300 or the sample number corresponding to "X".

Step 414 then retrieves the selected analytical method. In the preferred embodiment, the method instructions retrieved from the floppy disk in step 414 also include the appropriate instructions for initialing the liquid chromatograph and for equilibrating the column in accordance with the selected method. That is to say, each analytical method for analyzing a sample typically requires a specific procedure for initializing the liquid chromatograph and for equilibrating the column. In the prior art, such procedures had to be developed by a skilled operator, manually entered into the liquid chromatograph and then monitored and interpreted. with the present invention, however, such is not required, thereby eliminating the time and the skill for developing and entering the instructions. The program then moves to step 416 in order to initialize the liquid chromatograph and to equilibrate the column.

Step 418 runs the selected method for sample "X" and analyzes the spectrophotometric data obtained therefrom.

Figure 5:
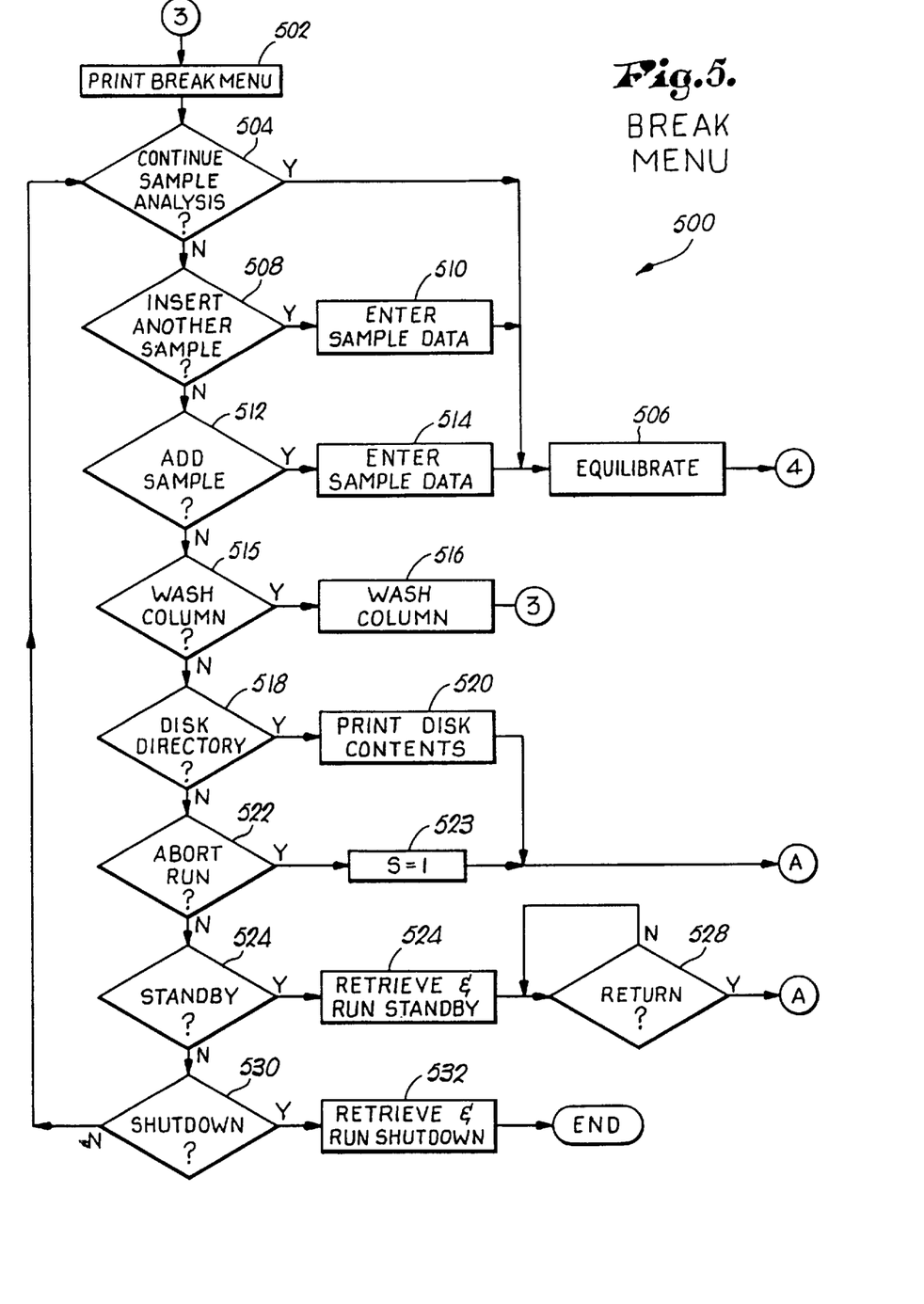
FIG. 5 is a computer program flow chart illustrating the BREAK MENU module of the operating program.

When the analysis is complete, the program moves to step 420 in order to print the analysis on printout 52 which typically includes the chromatogram and numerical data, and in the preferred embodiment, also includes the sample identification data. This provides a particularly useful printout which is in a finished format ready for presentation to the prescribing physician, for example, showing the sample identification data, the numerical data developed during the analysis, and the chromatogram itself Step 420 also stores this data for later use and retrieval. After each individual analysis in step 420, the program allows for intervention through step 421, which allows the operator to enter the BREAK MENU module 500, step 502.

If option 421 is not selected, the program next moves step 422 which asks whether variable S equals variable X which corresponds to the maximum number of samples. If no, which indicates that all of the samples in the series have not been analyzed, the program moves to step 424 which increments variable X and then loops back to perform steps 412–422 for the next sample in the series.

When the last sample has been analyzed, the answer in step 422 is yes, and the program moves to step 426 which asks whether the "standby" end-of-analysis mode has been selected. That is to say, this step asks whether the "standby" bit is active as set in step 402. If yes, the program moves to step 428 which retrieves and runs the standby instructions. This may include, for example, washing the column with a wash solution as described above. As those skilled in the art will appreciate, the particular requirements for standby are particular to column 12 and the mobile phases stored in reservoirs 28–32. The standby mode is typically selected when additional samples using the same method are to be analyzed within a short time.

After step 428, the program moves to step 430 and loops therearound until the return key is activated on the data entry keyboard. When such occurs, the program loops back to step 202 of the main menu submodule 200.

If the answer in step 426 is no, the program moves to step 432 which retrieves the shutdown instructions stored on the memory storage device. These instructions may include, for example, washing the column with a washing solution as described above but may additionally include other instructions such as shutting off pump 47 and de-energizing the lamp in detector 48. Again, the shutdown instructions are typically particular to the column type and mobile phases being used. The shutdown mode may be selected, for example, if completion of the analyses is not expected until after personnel quitting time. After step 432, the program ends.

FIG. 5 illustrates BREAK MENU module 500 which is entered after step 421. Module 500 enters at step 502 which prints the BREAK MENU item selections and the keyboard entry required to make the individual selections. The program then moves to step 504 which asks whether a selection has been entered to continue sample analyses. This might be selected, for example, if entry to BREAK MENU module 500 was selected in error. If yes, the program moves to step 506 to equilibrate the column. Column equilibration is usually required whenever an interruption in sample analysis occurs. After step 506, the program returns to SAMPLE ANALYSIS module 400 at step 424.

If the answer in step 504 is no, the program moves to step 506 which asks whether another sample is to be inserted as the next sample to be analyzed. This is particularly useful in a rush or so-called "STAT" situation in which it is desirable to immediately analyze a new sample without waiting until the end of the complete program. If the answer in step 508 is yes, the program moves to step 510 which prompts the operator to enter the appropriate sample data after which the program then moves on to step 506.

If the answer in step 508 is no, the program moves to step 512 which asks whether one or more samples are to be added to the end of the series. If yes, the program moves to step 514 which again prompts the operator to enter the appropriate sample data after which the program moves on to step 506.

If the answer in step 512 is no, the program moves to step 515 which asks whether the column is to be washed. If yes, the program moves to step 516 to be washed which retrieves the procedure for column washing from the floppy disk and then executes this procedure after which the program returns to BREAK MENU module 500.

If the answer in step 515 is no, the program asks whether the operator has selected "disk directory" from the menu. If yes, the program moves to step 520 to retrieve and print the data stored on the floppy disk. The program then returns to MAIN MENU module 200.

If the answer in step 518 is no, the program moves to step 522 which asks whether the sample analysis run is to be aborted. If yes, the program moves to step 523 which sets S=1. The program exits to MAIN MENU module 200.

If the answer in step 522 is no, the program asks whether the liquid chromatograph is to be put in a standby mode, step 524. If yes, the program retrieves and runs the standby instructions, step 526, and then waits in step 528 until the return key has been activated after which the program returns to MAIN MENU module 200.

If the answer in step 524 is no, the program moves to step 530 which asks whether the shutdown end-of-analysis mode has been selected. If yes, the program retrieves and executes the shutdown instructions in step 532 and the program execution ends.

As the description above indicates, the preferred operating program requires only that an operator initiate the program and enter data indicative of sample identification, method chosen and whether the liquid chromatograph is to be put in a standby or shutdown mode after completion of the analyses. None of these steps require particular technical knowledge in the operation of the liquid chromatograph and provide the additional benefit that once initiated, the operator's attendance and intervention are not required. Thus, the utility of the liquid chromatograph is greatly enhanced by allowing relatively unskilled operators to complete relatively sophisticated and complex analyses, and by greatly increasing productivity by eliminating the need for constant operator attention and intervention as is required with the prior art.

Actual analyses using the present invention demonstrate the effectiveness thereof. First of all, attention is directed to FIG. 8 which illustrates a chromatogram developed using only the preferred mobile phases of the invention. Note that the chromatogram is essentially a straight line with only minor deviations from an idealized baseline shown by dashed line. This is to be compared with FIG. 7, which shows the result using conventional mobile phases (the run conditions between FIGS. 7 and 8 are identical, as are such conditions between FIGS. 6 and 9).

Figure 9:
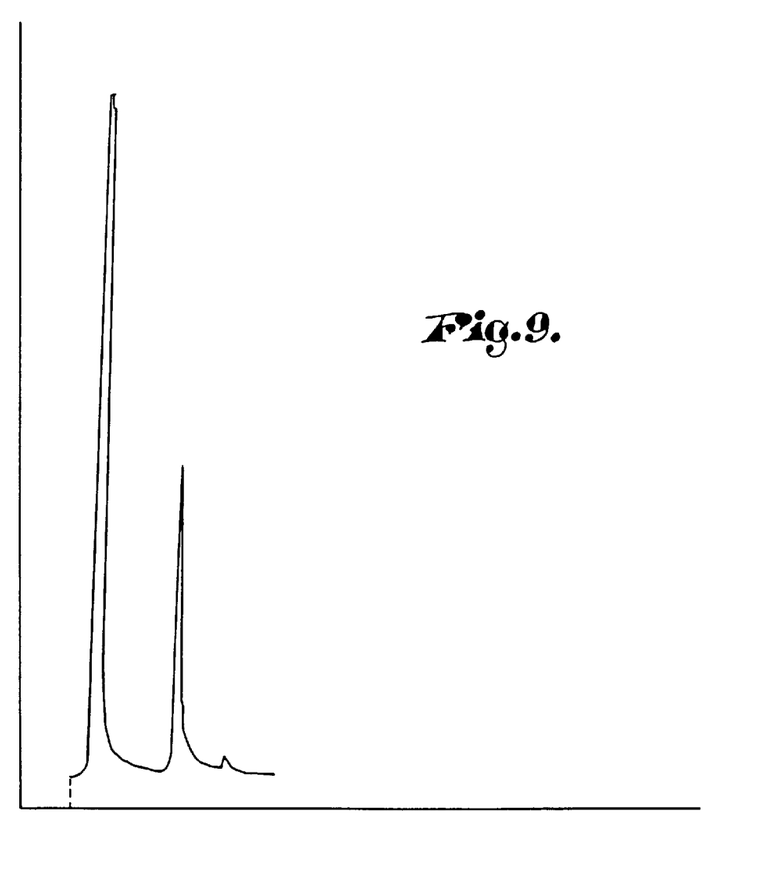
FIG. 9 is a chromatogram produced by automated HPLC equipment as a result of an analysis of a glycated serum protein sample using the preferred mobile phases of the invention.

FIG. 9 on the other hand is a chromatogram developed using the techniques of the invention during an analysis of the pooled sample described with reference to FIG. 6. In this case, however, the integrator error has been eliminated and the glycated serum protein is determined to be 13.6%, an accurate reading.

Figure 8:
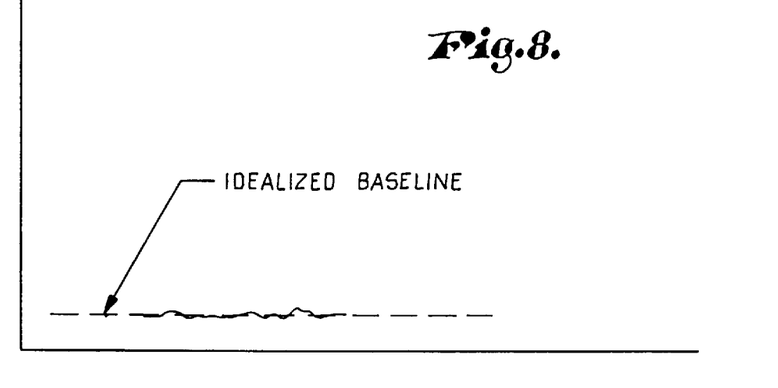
FIG. 8 is a chromatogram produced by automated HPLC equipment which depicts the absorbances of the preferred mobile phases of the invention.

As described earlier, a measure of the balance desired between the mobile phases A and B is the signal to noise ratio, making use of the idealized baseline generated from an analysis of the blank mobile phases (see FIG. 8). In the case of the present invention and the analyses depicted in FIGS. 8 and 9, the signal to noise ratio was determined to be 116. On the other hand, an identically determined signal to noise ratio in connection with the conventional mobile phases (FIGS. 6 and 7) gave a result of 1.022.

We claim:

1. A method of continuously and sequentially analyzing a plurality of liquid samples each containing both glycated and non-glycated blood protein fractions in respective blood-derived analytes forming a part of said samples using high pressure liquid chromatographic separation techniques, said method comprising the steps of:

(a) providing a boronate affinity high pressure liquid chromatographic column comprising hydroxyboryl moeities bound on a support;

(b) contacting said column with a respective liquid sample containing from 3.38–181.3 micrograms of said blood-derived analytes therein with a transport solution for said non-glycated protein fraction, said transport solution containing a buffering agent and a salt, causing said glycated protein fraction of said respective liquid sample to complex with said bound hydroxyboryl moeities, and separating the transport solution and the non-glycated protein fraction of said respective liquid sample from the column as a non-glycated protein analyzable mixture, said contacting steps being carried out at superatmospheric column pressure;

(c) spectrophotometrically analyzing said non-glycated protein analyzable mixture; and (d) repeating steps (b) and (c) to provide an analysis of each of said plurality of samples, with the total time between successive initial contacts of respective liquid samples with said column being no greater than about 8 minutes.

2. The method of claim 1, including the steps of contacting said column and complexed glycated proteins with an eluant for separating the glycated proteins from the column, separating the eluant and the separated glycated proteins from the column as a glycated protein analyzable mixture, and spectrophotometrically analyzing said glycated protein analyzable mixture.

3. The method of claim 2, including the steps of sequentially analyzing said non-glycated protein analyzable mixture and said glycated protein analyzable mixture.

* * * * *